(12) United States Patent
Kimhi et al.

(10) Patent No.: US 10,293,079 B2
(45) Date of Patent: May 21, 2019

(54) BIOLOGICAL ADHESIVES AND SEALANTS AND METHODS OF USING THE SAME

(71) Applicant: SEALANTIS LTD., Haifa (IL)

(72) Inventors: Ohad Kimhi, Kiryat Yam (IL); Ronit Langzam-Sinai, Kiryat Tivon (IL); Havazelet Bianco-Peled, Tivon Mail (IL); Charles Milgrom, Moshav Aminadav (IL); Rina Lev, Haifa (IL)

(73) Assignee: SEALANTIS LTD., Haifa (IL)

( * ) Notice: Subject to any disclaimer, the term of this patent is extended or adjusted under 35 U.S.C. 154(b) by 0 days.

(21) Appl. No.: 15/309,257

(22) PCT Filed: May 5, 2015

(86) PCT No.: PCT/IL2015/050473
§ 371 (c)(1),
(2) Date: Nov. 7, 2016

(87) PCT Pub. No.: WO2015/170327
PCT Pub. Date: Nov. 12, 2015

(65) Prior Publication Data
US 2017/0072094 A1 Mar. 16, 2017

Related U.S. Application Data

(60) Provisional application No. 62/074,724, filed on Nov. 4, 2014, provisional application No. 61/988,463, filed on May 5, 2014.

(51) Int. Cl.
*A61L 24/00* (2006.01)
*A61L 24/02* (2006.01)
*A61L 24/08* (2006.01)

(52) U.S. Cl.
CPC ........... *A61L 24/08* (2013.01); *A61L 24/0015* (2013.01); *A61L 24/0031* (2013.01); *A61L 24/02* (2013.01);
(Continued)

(58) Field of Classification Search
CPC ...... A61L 24/08; A61L 24/02; A61L 24/0015; A61L 24/0031; A61L 2300/802;
(Continued)

(56) References Cited

U.S. PATENT DOCUMENTS

| 5,266,326 | A | 11/1993 | Barry et al. |
| 6,124,373 | A | 9/2000 | Peter et al. |
| 6,150,581 | A | 11/2000 | Jiang et al. |
| 6,693,089 | B1 | 2/2004 | Li et al. |

(Continued)

FOREIGN PATENT DOCUMENTS

| CA | 2670429 A1 | 6/2008 |
| WO | 2010117266 A1 | 10/2010 |

(Continued)

OTHER PUBLICATIONS

International Search Report and Written Opinion for PCT/IL2015/050473 Completed Aug. 12, 2015; dated Aug. 26, 2015 12 Pages.

(Continued)

*Primary Examiner* — Robert A Wax
*Assistant Examiner* — Quanglong N Truong
(74) *Attorney, Agent, or Firm* — The Roy Gross Law Firm, LLC; Roy Gross

(57) ABSTRACT

This invention provides a kit for making an adhesive and/or a sealant which includes: a first composition of alginate and a multivalent cation salt at a concentration ratio (mg/ml) of 30:1 to 1:60, and a second composition of alginate and a buffer, wherein the buffer has a pH value of between 2 to 7. The invention also provides a method for making a sealant or an adhesive, by contacting the first composition and the second composition.

20 Claims, 5 Drawing Sheets

(52) U.S. Cl.
CPC ... *A61L 2300/232* (2013.01); *A61L 2300/412* (2013.01); *A61L 2300/424* (2013.01); *A61L 2300/802* (2013.01)

(58) Field of Classification Search
CPC ......... A61L 2300/424; A61L 2300/412; A61L 2300/232
See application file for complete search history.

(56) References Cited

U.S. PATENT DOCUMENTS

| | | | |
|---|---|---|---|
| 2002/0022676 A1 | 2/2002 | He et al. | |
| 2003/0175327 A1 | 9/2003 | Cochrum et al. | |
| 2005/0069589 A1* | 3/2005 | Lowinger | A61L 24/102 424/488 |
| 2006/0115511 A1 | 6/2006 | Zhang et al. | |
| 2007/0087038 A1* | 4/2007 | Richardson | A61K 9/0065 424/439 |
| 2010/0303891 A1 | 12/2010 | Lee et al. | |
| 2010/0316577 A1* | 12/2010 | Raineau | A61K 8/19 424/44 |

FOREIGN PATENT DOCUMENTS

| | | | |
|---|---|---|---|
| WO | 2010140146 A2 | 12/2010 | |
| WO | 2010146582 A2 | 12/2010 | |
| WO | WO-2010140146 A2 * | 12/2010 | ......... A61L 24/0015 |

OTHER PUBLICATIONS

"Multiple steps and critical behaviors of the binding of calcium to alginate." The Journal of Physical Chemistry, B, 2007, 111.10: 2456-2462. Frang, Yapeng, et al. Jan. 19, 2007 (Jan. 19, 2007).

A.A.Chaturvedi et al: "Prevention of postsurgical adhesions using an ultrapure alginate-based gel"; British Journal of Surgery, 2013; 100: 904-910.

A.A.Chaturvedi et al: "Ultrapure alginate anti-adhesion gel does not impair colon anastomotic strength"; Journal of Surgical Research 192, Jun. 4, 2014, pp. 432-439.

Fang, Y. et al: "Multiple Steps and Critical Behaviors of the Binding of Calcium to Alginate", The Journal of Physical Chemistry B, vol. 111, No. 10, pp. 2456-2462, Mar. 15, 2007.

* cited by examiner

Alginate Treated Operated Rotator Cuff in Rat
Alginate material is noted in-between the Deltoid muscle layer. The area of fibrosis is limited (10±2 days post-op)

Untreated Operated Rotator Cuff in Rat
Extensive area of the fibrotic (scar) tissue is noted in the Deltoid muscle, surrounding the Humerus bone (10±2 days post-op)

BIOLOGICAL ADHESIVES AND SEALANTS AND METHODS OF USING THE SAME

RELATED APPLICATIONS

This application is a National Phase of PCT Patent Application No. PCT/IL2015/050473 having International filing date of May 5, 2015, which claims the benefit of priority of U.S. Patent Application No. 61/988,463 filed on May 5, 2014 and 62/074,724 filed on Nov. 4, 2014. The contents of the above applications are all incorporated by reference as if fully set forth herein in their entirety.

FIELD OF INVENTION

This invention is directed to, inter alia, biological adhesives and sealants and methods of making and using the same.

BACKGROUND OF THE INVENTION

Adhesives and Sealants

Surgical adhesives have been increasingly used to enhance or at least partially replace traditional wound closure technologies such as sutures and staples, offering improved sealing capabilities and plugging of undesired leaks.

Despite recent developments and increased clinical demand, most of the currently available products suffer from serious drawbacks. One of the drawbacks is the short time-window available for their proper application onto the treated site and another is the short time they remain adhesive after application.

United States Application Publication No. US2005069589 to Lowinger et al. describes a tissue adhesive sealant that includes a cross-linkable protein in a solution, that when combined with a cross-linking agent solution including an aldehyde and amino acid containing species reactive with the aldehyde, cross-links to form a seal.

The sealant is stated to be highly suitable for bonding tissue alone or in combination with a patch. Such a system may not be easy to use as it may limit the time-window for application of the adhesive.

International Application Publication No. WO2010146582 is directed to reinforced multi component adhesives that include an uncured and curable spreadable composition of matter, and a biocompatible inert reinforcing agent including at least one curing agent, wherein the uncured composition applied to a surface is characterized as capable of curing after adding the reinforcing agent to the uncured composition, and wherein the cured composition together with the added reinforcing agent is configured to have improved mechanical support and strength. Following placement of the fibrous component containing the curing-agent, curing process begins spontaneously. The method and system of WO2010146582 provides the ability to control the time of application of the adhesive since the second step of applying the reinforcing agent is fully controlled by the caregiver, and curing occurs only once this second step is practiced.

However, a drawback of this method may be that curing often occurs immediately upon application of the reinforcing agent. As an example, if the curable composition contains albumin and the reinforcing agent contains gluteraldehyde, the crosslinking reaction will be initiated immediately after creating contact between albumin and gluteraldehyde. As a result, the caregiver cannot improve or alter the positioning of the reinforcing agent on the surface once applied.

United States Application Publication No. US2010303891 describes a biocompatible layer that specifically delays the release of NO as an agent.

U.S. Pat. No. 6,124,373 describes a method for controlling the gelling point of a bone cement containing poly (polypropylene fumarate), a cross-linking monomer, an initiator, an inorganic filler, and a radical initiator. The gelling point is controlled by varying the molecular weight of the poly(polypropylene fumarate) while maintaining the weight average molecular weight (Mw) of the poly(polypropylene fumarate) above 2000 and the polydispersity index of the poly(polypropylene fumarate) below 2.

United States Application Publication No. US2003175327 describes haemostatic compositions useful to promote hemostasis at active bleeding wound sites. The haemostatic compositions typically include an article containing cellulose, e.g., cotton gauze, and a polysaccharide covalently linked to the cellulose, or a polysaccharide ionically cross-linked and in association with the article. Obviously, the compositions have to be capable of immediate action upon application at the bleeding site, rather than controlled action after application, and thus the compositions are prepared ex-situ and ready for use in final form well before needed. Some of the compositions include cross-linked dextran beads that incorporate cations such as $Ca^{2+}$. The incorporated cations serve to promote haemostasis. The polysaccharides also serve to establish haemostasis, by size-excluding coagulation components. Additional materials may be added to make the composition adhesive.

Canadian Patent No. CA2670429 describes a gelling sealant for a medical device, the gelling sealant including: a viscoelastic material exhibiting a first viscosity during introduction into a body cavity; and a second viscosity after dwelling within the body cavity for a predetermined amount of time, the body cavity is adjacent to a medical device adapted to occlude at least a portion of the body cavity; wherein the viscoelastic material provides enhanced impermeability to the portion of the body cavity occluded by the medical device. The gelling sealant may thicken and then adhere to the inner surfaces of the body cavity after dwelling within the body cavity for a predetermined amount of time. Thickening results from crosslinks is described as being initiated by: mixing two components that are physically separated until combined in situ, or a prevalent condition in the physiological environment, such as temperature, pH, ionic strength, etc., and the cross-linking reaction rate and final viscosity are described as being dependent upon the concentration of cations in the solution.

Similarly, United States Application Publication No. US2002022676, describes in situ crosslinkable biodegradable polymer compositions which include poly(propylene fumarate) (PPF), poly(ethylene glycol)-dimethacrylate (PEG-DMA), and optionally, beta-tricalcium phosphate) beta-TCP), and a method for controlling the crosslinking characteristics of the compositions, including the optimal crosslinking temperature and the gel point, as well as the properties of the cross linked compositions such as the compressive strength and modulus and the water holding capacity. The gelling point and temperature are controlled by the amount of PEG in the composites.

Adhesion Barriers

Postoperative stiffness is one of the most common complications of shoulder surgery and is associated with pain, formation of adhesions, and limitation in motion. The pathophysiology of the stiffness complication is likely to be attributable to formation of adhesions primarily developing between the deltoid muscle and the underlying rotator cuff, in the extra-articular space. These occur frequently in cases of open anterior surgical approach to the shoulder (i.e., open reduction and internal fixation of shoulder fractures, Latarjet procedures, hemi- or total shoulder arthroplasties), and to a less extent in arthroscopic rotator cuff repairs or arthroscopic shoulder stabilizations (i.e., Bankart procedures). If the adhesion area is very small, physical therapy may be effective in "breaking" of adhesions. It is not effective, however, in the treatment of large area adhesions. Adhesions may also occur in shoulder fractures not treated surgically or secondary to blunt shoulder trauma. Other joints such as the elbow and knee can be similarly affected. Up-to-date, none of commercial adhesion prevention products, currently used in pelvic and abdominal surgeries, are available for adhesion prevention after rotator cuff repair surgeries, open reduction and internal fixation of shoulder fractures, Latarjet procedures, hemi- or total shoulders, arthroscopic Bankart procedures, blunt shoulder trauma, non surgically treated, shoulder fractures, elbow trauma or trauma or surgery about the knee.

A possible solution to prevent the formation of post-operative adhesions is the use of a mechanical barrier to prevent contact between the damaged muscle layers, and enable tissue healing with minimal scar formation. Currently, there is a range of adhesion prevention products, such as Interceed (J&J), Seprafilm etc., used in pelvic and abdominal surgical procedures (Ahmad G, et al. Cochrane Database Syst Rev. 2008 Apr. 16; (2)).

The use of alginate as a promising biomaterial in terms of adhesion prevention has been recently proposed (Chaturvedi A A, et al. Br J Surg. 2013 June; 100(7):904-10; Chaturvedi A. A., et al. J Surg Res. 2014 Jun. 4. pii: S0022-4804(14) 00548-4). In animal models, alginate gels have been reported to attenuate postoperative intraperitoneal adhesions following caecal abrasion (Chaturvedi 2013, ibid.) and repair of colon anastomoses (Chaturvedi 2014, ibid.). However, none of the aforementioned materials have been designed and used for adhesion prevention after rotator cuff repair surgeries, open shoulder surgery, blunt shoulder trauma, shoulder fractures, elbow trauma or trauma or surgeries about the knee.

U.S. Pat. No. 5,266,326 describes a method of modifying salts of alginic acid in situ, to form an insoluble gel, for prevention and treatment of various intra-articular and extra-articular (spine) complications.

U.S. Pat. No. 6,693,089 describes a method of reducing adhesion at a site of trauma, which includes forming a film from an alginate solution, contacting the film with a cross-linking solution to form a cross-linked mechanically stable sheet, and placing at least a portion of the sheet at the site of trauma. U.S. Pat. No. 6,693,089 further relates to an anti-adhesion barrier including a sheet of ionically cross-linked alginate having a thickness in a range of 0.25 mm to 10 mm.

International Application Publication No. WO 2010/117266 relates to a dispensing system that can be used to introduce a gel-forming fluid into or onto the body that will produce a homogeneous gel in situ.

SUMMARY OF THE INVENTION

In one embodiment, the present invention provides a kit comprising: a first component and a second component, wherein the first component comprises alginate and a multivalent cation salt at a concentration ratio (mg/ml) of 30:1 to 1:60, wherein the second component comprises alginate and a buffer or a buffering agent, wherein the buffer or buffering agent has a pH value of between 2 to 7 and comprises an acid and its acid addition salt. In some embodiments, the kit further comprises an instruction manual. In some embodiments, the alginate and the bivalent cation salt are at a concentration ratio (mg/ml) of 3:1 to 1:6. In some embodiments, the alginate and the multivalent cation salt are at a concentration ratio (mg/ml) of 1:1 to 1:4. In some embodiments, the buffer has a pH value of between 4 to 5. In some embodiments, the buffer is buffer acetate. In some embodiments, the concentration of the multivalent cation salt in the first component is 1.5 to 10 times higher than the stoichiometric ratio of the buffer (the salt within the buffer) having a concentration of between 1 to 2000 mM or alternatively 100 to 500 mM. In some embodiments, the multivalent cation salt has a particle size of between 0.1 microns and 150 microns.

In another embodiment, the present invention further provides a method for forming an adhesive and/or sealant, comprising contacting a first composition and a second composition, wherein the first composition comprises alginate and a multivalent cation salt at a concentration ratio (mg/ml) of 30:1 to 1:60, wherein the second composition comprises alginate and a buffer, wherein the buffer has a pH value of between 2 to 7 and comprises an acid and its acid addition salt, thereby forming a sealant.

In another embodiment, the present invention further provides a method for preventing, inhibiting, or reducing fibrosis, scarring, and/or adhesion in a target site, the method comprising the step of: (a) providing a first composition and a second composition, said first composition comprises a crosslinkable polysaccharide and a multivalent cation salt at a concentration ratio (mg/ml) of 30:1 to 1:60, said second composition comprises a crosslinkable polysaccharide and a buffer, said buffer has a pH value of between 2 to 7 and comprises an acid and its acid addition salt, (b) applying said first composition and said second composition to the target site thereby forming an adhesion barrier in situ, wherein said adhesion barrier adheres to said target site.

In another embodiment, the present invention further provides a sealant or an adhesion barrier produced by mixing a first composition comprising alginate and a bivalent cation salt at a concentration ratio (mg/ml) of 30:1 to 1:60 and a second composition comprising alginate and a buffer, wherein the buffer has a pH value of between 2 to 7 and comprises an acid and its acid addition salt.

DETAILED DESCRIPTION OF THE INVENTION

Figure 1:
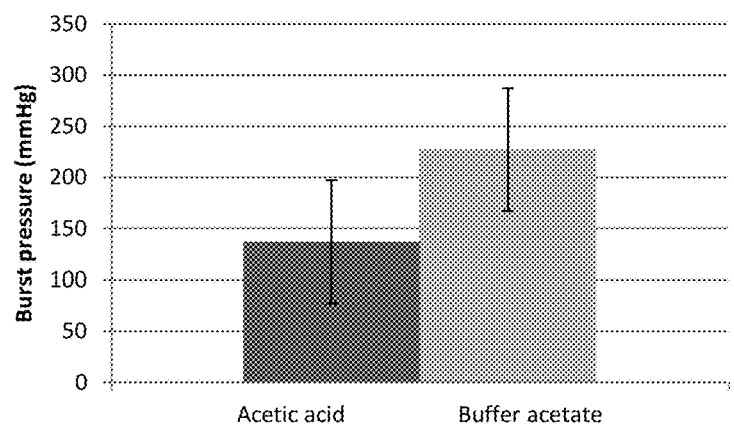
FIG. 1 is a bar graph showing the burst pressure of the double liquid sealant using acetic acid or buffer acetate.

In one embodiment, the present invention provides at least two distinct, separate, components (e.g., compositions of matter) that upon contact form a bio-absorbable adhesive. The adhesive, in some embodiments, may be adapted for internal use and be capable of adhering to wet as well as dry surfaces and tissues. In another embodiment, the adhesive is utilized as an integument curing agent. "Integument" according to the present invention is any layer that protects a tissue or an organ. "Integument" according to additional embodiments, is any layer or tissue that surrounds another tissue. In another embodiment, "integument" is skin, connective tissue, or mucous.

The present invention provides kits, methods and compositions based on extensive research that resulted in unexpected results. Specifically, the present invention provides that actuating/triggering a multivalent cation within a composition comprising alginate with a buffer (the second composition) results in a superior sealant with respect to the sealant's physical properties, the ability to control the cross-linking-gelation of the pre-sealant, and with respect to its uniformity. A pre-sealant, according to some embodiments, is a composition comprising alginate and an inactive multivalent cation. An inactive multivalent cation according to some embodiments is in the form of a salt of a multivalent cation such as a calcium salt. An inactive multivalent cation according to some embodiments cannot activate crosslinking/gelation of alginate. An inactive multivalent cation according to some embodiments is insoluble in a composition comprising alginate. The buffer of the invention activates the inactive multivalent cation upon contacting it.

In another embodiment, the present invention provides unexpected means for controlling gelation/crosslinking time. In another embodiment, the present invention provides unexpected means for controlling the physical properties of the adhesive of the invention. Physical properties of the adhesive, according to an embodiment of the invention, include but are not limited to burst pressure and the strain of break.

In another embodiment, unexpected means for controlling gelation/crosslinking time and unexpected means for controlling the physical properties of the adhesive (a crosslinked gel) include but are not limited to: the particle size of the salt of the multivalent cation, the identity of the salt of the multivalent cation, the type of buffer, the buffer's pH value, the concentration of acid within the buffer, the concentration of the salt of the multivalent cation, the concentration of alginate, the ratio between the salt of the multivalent cation and the salt and/or acid within the buffer, or any combinations thereof.

In another embodiment, the present invention provides two liquid compositions: the first includes alginate and an inactive multivalent cation salt (e.g., calcium salt) such as but not limited to $CaCO_3$, the second includes alginate and buffer such as but not limited to acetate. In another embodiment, liquid is aqueous. In one embodiment, the present invention provides two water based compositions.

In one embodiment, the present invention provides a kit comprising: a first component (e.g., composition), a second component (e.g., composition), and optionally an instruction manual, wherein first component comprises alginate and a calcium salt (inactive), and wherein the second component comprises alginate and a buffer.

One skilled in the art will appreciate that the first component and/or the second component may each take a form of a composition, or alternatively may be stored in separate containers, e.g., a double-chambered syringe, suitable for mixing two or more ingredients so as to form a composition. Accordingly, the terms "first component" and "second component" are used herein interchangeably with "first composition" and "second compositions", respectively.

One skilled in the art will appreciate that many suitable double-chambered syringes may be used for storing the ingredients of the adhesive of the invention prior to mixing and applying at a target site.

In one embodiment, the alginate and multivalent cation salt of the first component form a composition. In another embodiment, the alginate and multivalent cation salt of the first component are stored in separate containers. In another embodiment, the alginate and buffer or buffering agent of the second component form a composition. In another embodiment, the alginate and buffer or buffering agent of the second component are stored in separate containers.

In another embodiment, the buffer or buffering agent comprises an acid and its acid addition salt. In another embodiment, the buffer has a pH value of between 2 to 7. In another embodiment, the buffer has a pH value of between 3.5 to 6. In another embodiment, the buffer has a pH value of between 4 to 6. In another embodiment, the buffer has a pH value of between 4 to 5. In another embodiment, the buffer has a pH value of between 4.4 to 4.6. In another embodiment, the buffer has a pH value of 4.5.

In some embodiments, the first composition comprises alginate and a calcium salt at a concentration ratio (mg/ml) of 4:1 to 1:8. In some embodiments, the first composition comprises alginate and a calcium salt at a concentration ratio (mg/ml) of 2:1 to 1:4. In some embodiments, the first composition comprises alginate and a calcium salt at a concentration ratio (mg/ml) of 1:1 to 1:4. In some embodiments, the first composition comprises alginate and a calcium salt at a concentration ratio (mg/ml) of 1:1 to 1:3. In some embodiments, the first composition comprises alginate and a calcium salt at a concentration ratio (mg/ml) of 1:1 to 1:2.

In another embodiment, a crosslinkable polysaccharide is any polysaccharide that can be crosslinked. In another embodiment, a crosslinkable polysaccharide is any polysaccharide that can be crosslinked by a soluble divalent cation. In another embodiment, a crosslinkable polysaccharide is gelatin. In another embodiment, a crosslinkable polysaccharide is pectin. Cross linking (gelation) of crosslinkable polysaccharides such as but not limited to: alginates, is based on their affinity toward multivalent cations and their ability to bind those ions selectively and cooperatively, a process which leads to the formation of ionically cross linked alginate gels.

In some embodiments, alginate is Protanal LF 200 S (FMC Biopolymers) with G content of approximately 70% or Protanal HF 120 RBS with G content of approximately 50% (FMC Biopolymers). In some embodiments, alginate is any alginate known to one of average skill in the art.

In some embodiments, said multivalent cation salt is a bivalent cation salt. In another embodiment, the term "bivalent cation" is synonymous with the term "divalent cation". None limiting examples of bivalent cations include $Pb^{2+}$, $Cu^{2+}$, $Cd^{2+}$, $Ba^{2+}$, $Sr^{2+}$, $Co^{2+}$, $Ni_{2+}$, $Zn2+$ or $Mn^{2+}$. None limiting examples of trivalent cations includ $Al^{3+}$ or $Fe^{3+}$.

In some embodiments, said bivalent cation salt is calcium salt. In some embodiments, calcium salt is $CaCO_3$. In some embodiments, calcium salt is $(C_{17}H_{35}COO)_2Ca$. In some embodiments, calcium salt is $CaCO_3$. In some embodiments, calcium salt is $CaNa_2P_2O_7$. In some embodiments, calcium salt is $Ca_2P_2O_7$. In another embodiment, calcium salt is any combination of $CaCO_3$, $(C_{17}H_{35}COO)_2Ca$, $CaNa_2P_2O_7$, $Ca_2P_2O_7$, wherein each possibility is a separate embodiment of the present invention.

In some embodiments, said bivalent cation salt is barium salt. In some embodiments, calcium salt is $BaCO_3$.

In another embodiment, alginate is present at a concentration of 5 to 100 mg/ml within the first composition. In another embodiment, alginate is present at a concentration of 5 to 70 mg/ml within the first composition. In another embodiment, alginate is present at a concentration of 10 to 60 mg/ml within the first composition. In another embodiment, alginate is present at a concentration of 10 to 40 mg/ml within the first composition. In another embodiment, alginate is present at a concentration of 10 to 30 mg/ml within the first composition. In another embodiment, alginate is present at a concentration of 15 to 25 mg/ml within the first composition. In another embodiment, alginate is present at a concentration of 20 mg/ml within the first composition.

In another embodiment, alginate is present at a concentration of 5 to 100 mg/ml within the first composition. In another embodiment, alginate is present at a concentration of 5 to 70 mg/ml within the second composition. In another embodiment, alginate is present at a concentration of 10 to 60 mg/ml within the second composition. In another embodiment, alginate is present at a concentration of 10 to 40 mg/ml within the second composition. In another embodiment, alginate is present at a concentration of 10 to 30 mg/ml within the second composition. In another embodiment, alginate is present at a concentration of 15 to 35 mg/ml within the second composition. In another embodiment, alginate is present at a concentration of 20 mg/ml within the second composition. In another embodiment, the concentration of alginate within the first composition and within the second composition is the same.

In another embodiment, the viscosity of the first composition and/or the second composition is between 100 cP and 100000 cP. In another embodiment, the viscosity of the first composition and/or the second composition is between 100 cP and 10000 cP. In another embodiment, the viscosity of the first composition and/or the second composition is between 100 cP and 1000 cP. In another embodiment, the viscosity of the first composition and/or the second composition is between 100 cP and 800 cP. In another embodiment, the viscosity of the first composition and/or the second composition is between 200 cP and 800 cP. In another embodiment, the viscosity of the first composition and/or the second composition is between 300 cP and 700 cP. In another embodiment, the viscosity of the first composition and/or the second composition is between 5000 cP and 100000 cP. In another embodiment, the viscosity of the first composition and/or the second composition is between 1000 cP and 70000 cP. In another embodiment, the viscosity of the first composition and/or the second composition is between 30000 cP and 80000 cP. In another embodiment, the viscosity of the first composition and/or the second composition is between 800 cP and 8000 cP. In another embodiment, the viscosity of the first composition and/or the second composition is between 1000 cP and 5000 cP.

In another embodiment, alginate is substituted with any water miscible cross-linkable polymer. In another embodiment, water miscible cross-linkable polymer is a naturally existing form of a carbohydrate. In another embodiment, water miscible cross-linkable polymer is synthetically prepared form of carbohydrate and a salt of a polysaccharide.

In another embodiment, water miscible cross-linkable polymer is a hydrophilic polymer selected from one of more of: polyethylene glycol, polyvinyl alcohol, alginate, collagen and dextran, and combinations thereof.

In another embodiment, alginate is present at a concentration of 5 to 50 mg/ml within the second composition. In another embodiment, alginate is present at a concentration of 10 to 40 mg/ml within the second composition. In another embodiment, alginate is present at a concentration of 10 to 30 mg/ml within the second composition. In another embodiment, alginate is present at a concentration of 15 to 25 mg/ml within the second composition. In another embodiment, alginate is present at a concentration of 20 mg/ml within the second composition.

In another embodiment, the salt of the multivalent cation is present at a concentration of 10 to 50 mg/ml within the first composition. In another embodiment, the salt of the multivalent cation is present at a concentration of 20 to 40 mg/ml within the first composition. In another embodiment, the salt of the multivalent cation is present at a concentration of 25 to 35 mg/ml within the first composition. In another embodiment, the salt of the multivalent cation is present at a concentration of 30 mg/ml within the first composition.

As used herein the terms "buffer" and "buffering agent" are used interchangeably, and refer to any compound and/or combination of compounds (e.g., in solid or liquid state), which will maintain the pH of the composition at a desired range. In another embodiment, the buffer has a pH value of between 3 to 6. In another embodiment, the buffer has a pH value of between 4 to 5. In another embodiment, the buffer has a pH value of between 4.2 to 4.8. In another embodiment, the buffer has a pH value of between 4.4 to 4.6.

In another embodiment, the buffer has a concentration of between 1 to 2000 mM. In another embodiment, the buffer has a concentration of between 1 to 1500 mM. In another embodiment, the buffer has a concentration of between 1 to 1000 mM. In another embodiment, the buffer has a concentration of between 1 to 500 mM. In another embodiment, the buffer has a concentration of between 50 to 500 mM. In another embodiment, the buffer has a concentration of between 100 to 500 mM. In another embodiment, the buffer has a concentration of between 150 to 400 mM. In another embodiment, the buffer has a concentration of between 200 to 400 mM. In another embodiment, the buffer has a concentration of between 250 to 300 mM. In another embodiment, the buffer has a concentration of 300 mM. In another embodiment, the buffer has a concentration of between 200 to 600 mM. In another embodiment, the buffer has a concentration of between 300 to 500 mM. In another embodiment, the buffer has a concentration of 400 mM.

In another embodiment, the buffer comprises 0.2 to 10% (by volume) acid. In another embodiment, the buffer comprises 0.2 to 9% (by volume) acid. In another embodiment, the buffer comprises 0.2 to 8% (by volume) acid. In another embodiment, the buffer comprises 0.2 to 7% (by volume) acid. In another embodiment, the buffer comprises 0.2 to 6% (by volume) acid. In another embodiment, the buffer comprises 0.2 to 5% (by volume) acid. In another embodiment, the buffer comprises 0.2 to 4% (by volume) acid. In another embodiment, the buffer comprises 0.2 to 3% (by volume) acid. In another embodiment, the buffer comprises 0.2 to 2% (by volume) acid. In another embodiment, the buffer comprises 1.5%-2% (by volume) acid. In another embodiment, the buffer comprises 0.2 to 1% (by volume) acid. In another embodiment, the buffer comprises 0.4 to 0.8% (by volume) acid. In another embodiment, the buffer comprises 0.4 to 0.6% (by volume) acid. In another embodiment, the buffer comprises 0.5% (by volume) acid. In another embodiment, the buffer comprises 1.7% (by volume) acid. In another embodiment, the acid is acetic acid. In another embodiment, the buffer comprises sodium acetate salt.

In another embodiment, the concentration of the multivalent cation salt (e.g., calcium salt) in the first composition is higher than the stoichiometric ratio of the buffer (or salt within the buffer) having a concentration of between 100 to 500 mM. In another embodiment, the concentration of the multivalent cation salt in the first composition is 1.5 to 10 times higher than the stoichiometric ratio of the buffer having a concentration of between 100 to 500 mM. In another embodiment, the concentration of the multivalent cation salt in the first composition is 1.5 to 8 times higher than the stoichiometric ratio of the buffer having a concentration of between 200 to 400 mM. In another embodiment, the concentration of the multivalent cation salt in the first composition is 1.5 to 5 times higher than the stoichiometric ratio of the buffer having a concentration of between 250 to 350 mM.

In another embodiment, the multivalent cation salt (e.g., calcium salt) has a particle size between 0.1 microns and 250 microns. In another embodiment, the multivalent cation salt (e.g., calcium salt) has a particle size between 0.1 microns and 150 microns. In another embodiment, the multivalent cation salt has a particle size between 0.1 microns and 100 microns. In another embodiment, the multivalent cation salt has a particle size between 0.1 microns and 50 microns. In another embodiment, the multivalent cation salt (e.g., calcium salt) has a particle size smaller than 50 microns. In another embodiment, multivalent cation salt has a particle size between 1 microns and 40 microns. In another embodiment, the multivalent cation salt has a particle size between 1 microns and 30 microns.

In another embodiment, calcium salt is $CaCO_3$ at a concentration of 20 to 40 mg/ml, alginate is present at a concentration of 10 to 30 mg/ml, the buffer is buffer acetate having a pH value between 4.4 to 4.6 and a concentration of between 1 to 500 mM. In another embodiment, calcium salt is $CaCO_3$ at a concentration of 20 to 40 mg/ml, alginate is present at a concentration of 10 to 30 mg/ml, the buffer is buffer acetate having a pH value between 4.4 to 4.6 and a concentration of between 100 to 400 mM.

In another embodiment, the instruction manual provides instructions with respect to quantities of the first composition and the second composition to be applied. In another embodiment, the instruction manual provides a spectrum of gelation time, wherein the gelation time is provided as any one of a function of the particle size of the calcium salt, the particular calcium salt to be used, the pH value of the buffer, or any combination thereof.

In another embodiment, the second composition is contacted with the first composition by spraying, dripping, or wetting the pre-gel (the second composition) with the second composition. In another embodiment, the pre-gel hardens (crosslinked) with time due to the dissolution of the multivalent salt.

In some embodiments, the present invention further provides a method for forming an adhesive/sealant, comprising contacting a first composition and a second composition, wherein the first composition comprises alginate and an inactive multivalent salt (inability to crosslink the alginate) at a concentration ratio (mg/ml) of 2:1 to 1:4, the second composition comprises alginate and a buffer, wherein the buffer has a pH value of between 3.5 to 6 and comprises an acid and its acid addition salt. In another embodiment, the identities of the constituents, concentrations, ratios, pH values, particle size, and amounts to be used according to the methods of the present invention are coherent with the kits as provided herein.

In some embodiments the adhesive/sealant is 10 microns to 8 mm thick. In another embodiment, the sealant is 100 microns to 1 mm thick. In another embodiment, the sealant is 50 microns to 500 microns thick. In another embodiment, the sealant is 200 microns to 500 microns thick. In another embodiment, the adhesive/sealant is up to 1 cm thick. One skilled in the art will appreciate that thickens of the adhesive/sealant depends, inter alia, on the mode of administration and the target site of the sealant/adhesive.

In another embodiment, forming a sealant further comprises controlling gelation time, wherein a pH value of the buffer of less than 4.5 increases gelation time and wherein smaller particle size of the calcium salt decreases gelation time.

In another embodiment, further provided herein is an adhesive/sealant produced or formed by contacting and/or mixing a first composition comprising alginate and a multivalent cation salt (e.g., calcium salt) at a concentration ratio (mg/ml) of 2:1 to 1:4 and a second composition comprising alginate and a buffer, wherein the buffer has a pH value of between 3.5 to 6 and comprises an acid and its acid addition salt.

The ability to control crosslinking according to the present invention is crucial for any medical use as the practitioner can control gelation/crosslinking rate according to the medical procedure being formed. In another embodiment, the ability to set crosslinking rate according to the present invention is crucial for any medical use as the practitioner can set the crosslinking rate suitable for the medical procedure being formed.

In another embodiment, it is important that the concentration of the salt of the multivalent cation (which is insoluble in the first liquid composition) is higher than its stoichiometry with the buffer. In another embodiment, a concentration of the salt of the multivalent cation higher than its stoichiometry with the buffer results in a stronger sealant. In another embodiment, a concentration of the salt of the multivalent cation higher than its stoichiometry with the buffer results in favorable sealant physical properties. In another embodiment, elevating the concentration of the salt of the multivalent cation beyond its stoichiometry with the buffer, results in a transparent/lucent adhesive/sealant (a property that can assist the caregiver with respect to visualizing the area where the adhesive/sealant is present).

In another embodiment, the second composition further comprises a surfactant that further solubilizes the salt of the multivalent cation (which is insoluble in the first liquid composition). In another embodiment, the surfactant is a biocompatible surfactant. In another embodiment, the surfactant is non-toxic in the concentration of the surfactant utilized.

Optionally, colorant or other components for controlling physical/chemical properties of the pre-gel (salts, preservatives, etc.) can be provided to any of the components of the adhesive.

In some embodiments, the present invention further provides that a method for forming a sealant (also synonymous with tissue adhesive) includes a method of producing a tissue adhesive that adheres to biological surfaces. In some embodiments, the adhesive/sealant becomes inert after curing (the result of the crosslinking and gelation process). In some embodiments, the present invention further provides that a method for forming an adhesive/sealant includes a method of in situ application (to a subject) of the first and second compositions as described herein. In another embodiment, the first composition is a pre-gel. In another embodiment, the "first composition" is synonymous with "pre-gel".

In another embodiment, a method as described herein includes: applying an uncured pre-gel to a bodily surface and subsequently contacting the uncured pre-gel with the second composition which allows the uncured pre-gel to cure (crosslink) and to become increasingly adhesive to the bodily surface.

In another embodiment, the present invention further provides a first composition and a second composition for forming an adhesive and/or sealant, wherein the first composition comprises alginate and a multivalent cation salt at a concentration ratio (mg/ml) of 30:1 to 1:60, and wherein the second composition comprises alginate and a buffer, wherein the buffer has a pH value of between 2 to 7 and comprises an acid and its acid addition salt. In one embodiment, said adhesive and/or sealant is formed upon contacting said first composition and said second composition.

According to some embodiments of the present invention, the uncured pre-gel is the source of cross-linking agents (multivalent cations). The multivalent cations and salts comprising the same are, in some embodiments, in a water-insoluble inactive form, such that as long as there no actuation/triggering (by the second composition comprising alginate and a buffer) of the inactive form no crosslinking can occur.

In some embodiments, the buffer within the second composition is the trigger factor. In another embodiment, the term "triggering" refers to the ability of the buffer to release a cross-linking agent from its insoluble form, such that the cross linking agent causes the uncured pre-gel to cure. In another embodiment, as a result of gaining cohesive strength the adhesive/sealant resulting from the addition of the second composition to the first composition is strongly bound/ adhered to a bodily or a biological surface.

In one embodiment, the adhesive is used for securing/ holding a graft, e.g., a bone graft, artificial bone graft or a bone healing promoter, in place for a predetermined time.

In another embodiment, the present invention further provides a method for securing or holding a graft in a target site, the method comprising the step of: (a) providing a first composition and a second composition, said first composition comprises a crosslinkable polysaccharide and a multivalent cation salt at a concentration ratio (mg/ml) of 30:1 to 1:60, said second composition comprises a crosslinkable polysaccharide and a buffer, said buffer has a pH value of between 2 to 7 and comprises an acid and its acid addition salt, (b) applying said first composition and said second composition to a graft situated at the target site, thereby securing or holding said graft at the target site.

In another embodiment, the present invention further provides a first composition and a second composition for forming an adhesion barrier in situ, said first composition comprises a crosslinkable polysaccharide and a multivalent cation salt at a concentration ratio (mg/ml) of 30:1 to 1:60, said second composition comprises a crosslinkable polysaccharide and a buffer, said buffer has a pH value of between 2 to 7 and comprises an acid and its acid addition salt. In one embodiment, said adhesion barrier prevents, inhibits, or reduces fibrosis, scarring, and/or adhesion in a target site.

In some embodiments of the invention, a solid support is further integrated with the sealant/adhesive by adding it to the first composition prior to curing (the addition of the second composition), to provide additional mechanical strength to the sealant/adhesive.

In another embodiment, the sealant is a surgical multi component adhesive suitable for internal use in a subject. The adhesive, in some embodiment, is bio-absorbable. In another embodiment, the adhesive/sealant is absorbed into the body of the patient within a period of 3 days to 6 months. In another embodiment, the adhesive/sealant is absorbed into the body of the patient within a period of 1 to 18 weeks. In another embodiment, the adhesive/sealant is absorbed into the body of the patient within a period of 2 to 12 weeks.

According to one embodiment, a multi component adhesive is provided that comprises: 1. An uncured pre-gel including a solution of cross-linkable polysaccharide, such as alginate. The pre-gel may be lightly cross-linked, yet it is still substantially fluid and easily administrable to a surface. 2. A second composition carrying a triggering buffer which activates-solubilizes the previously insoluble bivalent cation salt present within the uncured pre-gel (first composition). In another embodiment, the first composition is a dry uncured pre-gel including a dehydrated solution of cross-linkable polysaccharide, such as alginate.

Optionally, pharmaceutical substances such as antibacterial compounds, antiseptic compounds, drugs, anti-oxidants, growth factors, therapeutic proteins/peptides or other therapeutic molecules for wound healing, anti-cancer, anti-arrhythmia, etc. are incorporated within the first composition and/or second composition so as to be released from the adhesive/sealant within the area to be treated.

In some embodiments, the second composition is contacted with the first composition at a site to be sealed/ adhered. In some embodiments, contacting the second and the first composition is embedding, mixing, blending or even laying the second composition on top of the first composition.

In another embodiment, a layer of pre-gel is spread or applied on the tissue or the bodily surface and the second composition is then contacted with the layer of the pre-gel. In another embodiment, the pre-gel hardens (being cross-linked) due to the de-novo solubilization of the multivalent salt.

The Application of the Sealant

Several methods are used to apply sealant in the site that requires tissue repair or tissue sealing. (1) A layer of a liquid pre-gel (comprising an inactive form of a crosslinking agent, for example insoluble salt of multivalent ions (e.g. $CaCO_3$ or CaEGTA)) is spread on the bodily surface, and then the second composition is contacted with the pre-gel thus forming a sealant. (2) A layer of a dry pre-gel is placed on the bodily surface, and then the second composition is contacted with the pre-gel thus forming an adhesive/sealant. In some embodiments, liquids, such as saline, are further applied to the site. The caregiver, in some embodiments, uses a particular buffer and/or particular multivalent salt for controlling the time period for hardening (curing, crosslinking) process which renders the combination of the first composition and the second composition as an adhesive/sealant. In another embodiment, once the pre-gel is cured (crosslinked), it loses its adherence capability thus acts as a barrier/sealant.

Adhesion Barriers

In another embodiment, the present invention provides kits, methods and compositions for forming an adhesion barrier used to reduce adhesions in a target site, including but not limited to traumatized tissue such as following surgery. The adhesion barrier disclosed herein adheres to the target site in situ. In some embodiments, said adhesion barrier separates said tissues during the tissue healing process.

The present invention is based, in part, on the finding that alginate-based formulations disclosed herein, can be used as adhesion barriers, such as in traumatized tissue. As demonstrated hereinbelow, the capability of alginate-based formulations of the present invention to perform as adhesion barrier in reduction of postoperative shoulder stiffness after surgical trauma was assessed in a rat model. At completion of the experiments, passive shoulder mechanics, based on angular range of motion (ROM) measurements, were recorded on the operated shoulders in comparison with the non-operated shoulder. None to minimal reduction in the total ROM and negligible shoulder stiffness were found in alginate-treated animals, as compared to control animals having restricted passive ROM and notable shoulder stiffness, postoperatively.

In another embodiment, the present invention provides a method for preventing, inhibiting or reducing fibrosis, scarring and/or adhesion in a target site, the method comprising the step of:

(a) providing a first composition and a second composition, said first composition comprises a crosslinkable polysaccharide and a bivalent cation salt at a concentration ratio (mg/ml) of 3:1 to 1:6, said second composition comprises a crosslinkable polysaccharide and a buffer, said buffer has a pH value of between 2 to 7 and comprises an acid and its acid addition salt, (b) applying said first composition and said second composition to the target site, thereby forming, in situ, an adhesion barrier adherent to said target site, thereby preventing, inhibiting or reducing fibrosis, scarring and/or adhesion of said traumatized tissues In another embodiment, the method of the invention further comprising the step of mixing said first composition and said second composition prior to applying said compositions to the traumatized tissue. According to some embodiments, said mixing step initiates gelation or crosslinking of said first composition and said second composition to an adhesive barrier.

In another embodiment, said target site is a surgical site. In another embodiment, said target site is a post-operative surgical site. In another embodiment, said fibrosis, scarring and/or adhesion results from a surgical procedure. In another embodiment, said fibrosis, scarring and/or adhesion results from blunt trauma or a fracture.

Adhesions are known in the art as abnormal, fibrous bands of scar tissue that can form inside the body as a result of the healing process that often follows open or minimally invasive surgical procedure including abdominal, gynecologic, cardiothoracic, spinal, plastic, vascular, ENT, ophthalmologic, urologic, neuro, or orthopedic surgery. Adhesions are typically connective tissue structures that form between adjacent injured areas within the body. Briefly, localized areas of injury trigger a healing response that culminates in healing and scar tissue formation. If scarring results in the formation of fibrous tissue bands or adherence of adjacent anatomical structures (that should normally be separate), adhesion formation is said to have occurred.

Post-surgical adhesions are a consequence resulting when injured or traumatized tissue surfaces, following incision, cauterization, suturing or other mechanical means of trauma, fuse together to form scar tissue. Adhesions can also occur in areas that have undergone blunt trauma or in tissue surrounding fractures. The mechanism of adhesion formation at a traumatized area is based on secretion of a tissue exudate, which in turn induces fibroblast proliferation and consequent formation of collagenous adhesions. These adhesions scar-up the tissue and lead to dysfunctional soft tissues.

Adhesion formation may occur following any surgery or trauma, and is a source of considerable morbidity. For example, postoperative intra-abdominal and pelvic adhesions are a leading cause of infertility, chronic pelvic pain, and intestinal obstruction. Adhesions forming in the tissue may also irritate surrounding nerves and disrupt nerve transmissions, resulting in a significant reduction of sensory or motor function.

In some embodiments, reducing adhesion includes a decrease in adhesion formation and does not require complete alleviation of adhesion signs or symptoms, and does not require a cure. In various embodiments, reducing adhesion formation includes even a marginal decrease in adhesion formation by for example at least 5%, 10%, 15%, 20%, 25%, 30%, 35%, 40%, 45% or higher decreases in adhesion formation or compared to control.

"Reducing adhesions" refers to administering the first and second compositions disclosed herein so as to cause a reduction in the number of adhesions, extent of adhesions (e.g., area), and/or severity of adhesions (e.g., thickness or resistance to mechanical or chemical disruption) relative to the number, extent, and/or severity of adhesions that would occur without such administration. In various embodiments, reducing adhesions may be part of a protocol and also include performing a procedure (e.g., subsequent surgery to reduce adhesions). The compositions or procedure may inhibit formation, or growth of adhesions following an adhesion promoting stimulus, may inhibit progression of adhesions, and/or may inhibit recurrence of adhesions following their spontaneous regression or following mechanical or chemical disruption.

"Preventing adhesions" refers to administering the first and second compositions prior to formation of adhesions in order to reduce the likelihood that adhesions will form in response to a particular insult, stimulus, or condition. In various embodiments, preventing adhesions may be part of a protocol and also include performing a procedure (e.g., surgery to reduce adhesions). It will be appreciated that "preventing adhesions" does not require that the likelihood of adhesion formation is reduced to zero. Instead, "preventing adhesions" refers to a clinically significant reduction in the likelihood of adhesion formation following a particular insult or stimulus, e.g., a clinically significant reduction in the incidence or number of adhesions in response to a particular adhesion promoting insult, condition, or stimulus.

In various embodiments, the adhesion barrier can act as an adhesion barrier that can be administered or applied to the target tissue site before, during or after the surgery to reduce, prevent or inhibit adhesions. In some embodiments, the adhesion barrier creates a barrier that separates opposing tissue surfaces or tissue-organ surfaces while injured or traumatized tissues heal. In growth of scar tissue and the formation or reformation of adhesions immediately adjacent to the adhesion barrier is thus prevented.

In another embodiment, said target site is a site of tissue injury including, but not limited to, sites of incision, drying, suturing, excision, abrasion, contusion, laceration, anastomosis, manipulation, prosthetic surgery, curettage, orthopedic surgery, neurosurgery, cardiovascular surgery, and plastic or reconstructive surgery. Target sites are also here understood to include neighboring undamaged tissue. In another embodiment, said target site is an area that has been exposed to blunt trauma or the soft tissue surrounding a fracture.

In some embodiment, the invention has application in various surgical procedures. In another embodiment, said surgical procedure is a gynecological surgical procedure (myomectomy via laparotomy or laparoscopy). According to non-limiting embodiments, during removal of a fibroid, an incision is made in the uterus, and a barrier can be formed in between the uterus and the surrounding tissues to prevent adhesion.

In another embodiment, said surgical procedure is abdominal surgery. According to non-limiting embodiments, an adhesion barrier can be used to prevent peritoneal adhesions and therefore prevent intestinal obstruction.

In another embodiment, said surgical procedure is cardiac surgery. According to non-limiting embodiments, a barrier can be used to prevent post-operative adhesion after cardiac procedures.

In another embodiment, said surgical procedure is craniofacial surgery. According to non-limiting embodiments, a barrier can protect the exposed cortex during craniotomy to prevent the skull and the cortex from adhering.

In another embodiment, said surgical procedure is musculoskeletal surgery. According to non-limiting embodiments, a barrier can prevent adherence of a tendon and the surrounding tissues.

In some embodiments, the adhesion barrier is biocompatible. i.e., does not cause substantial tissue irritation or necrosis at the target tissue site. It will be appreciated by those with skill in the art that the first and second composition (forming the adhesion barrier of the invention) can be administered to the target site using a "cannula" or "needle", e.g., a syringe, a gun drug delivery device, or any medical device. The cannula or needle is typically designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The dimensions of the hollow cannula or needle, among other things, will depend on the site for implantation.

In one embodiment, the term "comprise", and variations thereof such as "comprises", "comprising" and the like indicate that the components listed are included, but not generally to the exclusion of other components. In one embodiment, the term "comprise", and variations thereof such as "comprises", "comprising" and the like are substituted with the term "consist" and all variation of "consist".

In one embodiment, the amount of a sealant to be applied depends on the medical procedure that is being preformed, the severity of the affliction, and the judgment of the caregiver.

In one embodiment, the compositions for forming a sealant as described herein are provided to the individual per se. In one embodiment, a sealant as described herein can be provided to the individual with a pharmaceutical composition. In one embodiment, a pharmaceutical composition is mixed within a sealant as described herein. In one embodiment, a sealant as described herein is a drug carrier. In one embodiment, a sealant as described herein is an extended release drug carrier.

In one embodiment, a sealant as described herein is a "physiologically acceptable carrier" and/or a "pharmaceutically acceptable carrier". In another embodiment, additional carriers and/or polymers are incorporated into the sealant of the invention, such as but not limited to: polyethylene glycol (PEG), a biocompatible polymer with a wide range of solubility in both organic and aqueous media.

In one embodiment, the first composition, the second composition, or both further comprise an excipient. In some embodiments, "excipient" refers to an inert substance added any of the compositions described herein. In one embodiment, excipients may include calcium carbonate, calcium phosphate, various sugars and types of starch, cellulose derivatives, vegetable oils and polyethylene glycols.

In some embodiments, compositions as described herein include solutions or emulsions, which in some embodiments are aqueous solutions or emulsions. In some embodiments, a composition as described herein comprises from about 0.01% to about 10.0% w/v of an active pharmaceutical ingredient.

Further, in another embodiment, a sealant as described herein is used for administering, topically to body surfaces, an active pharmaceutical ingredient.

In one embodiment, compositions of the present invention are manufactured by processes well known in the art, e.g., by means of conventional mixing, dissolving, entrapping or lyophilizing processes.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives.

In another embodiment, the sealant of the invention is used as a controlled release system such as similarly to a transdermal patch, or other modes of administration.

In some embodiments, at least two composition as described herein are packed separately in kits. In some embodiments, each composition may comprise sterile, pyrogen-free water.

In another embodiment, the combined mix of the first and/or the second compositions is/are further dried and can be hydrated.

EXAMPLES

Example 1: Sealant Made of Two Distinct Compositions

The double liquid sealant results from contacting two components: the first included alginate (20 mg/ml) and CaCO$_3$ (30 mg/ml), the second component included alginate (20 mg/ml) and buffer acetate (acetic acid and sodium acetate salt) (pH 4.5 200 mM).

The buffer: FIG. 1 demonstrates the differences in the sealant performance; when the second component of the sealant included acetic acid 0.5% the burst pressure was surprisingly much lower than with buffer acetate pH 4.5 200 mM. The pH of the solution including acetic acid 0.5% was 4.2 and the pH of the buffer was 4.5, the pH values were similar and still, surprisingly, the resulting sealants were very different. Moreover, it seems that the actual use of a buffer and not an acid allowed the control over the reaction end point and gelation). Thus the use of a buffer provides controlled crosslinking. This feature is crucial when sealant is prepared during a medical procedure. The caregiver has an obvious interest in controlling the overall duration and rate of gelation in accordance to other procedures that are being performed in parallel at the site of the sealant or at a nearby locus.

Figure 2:
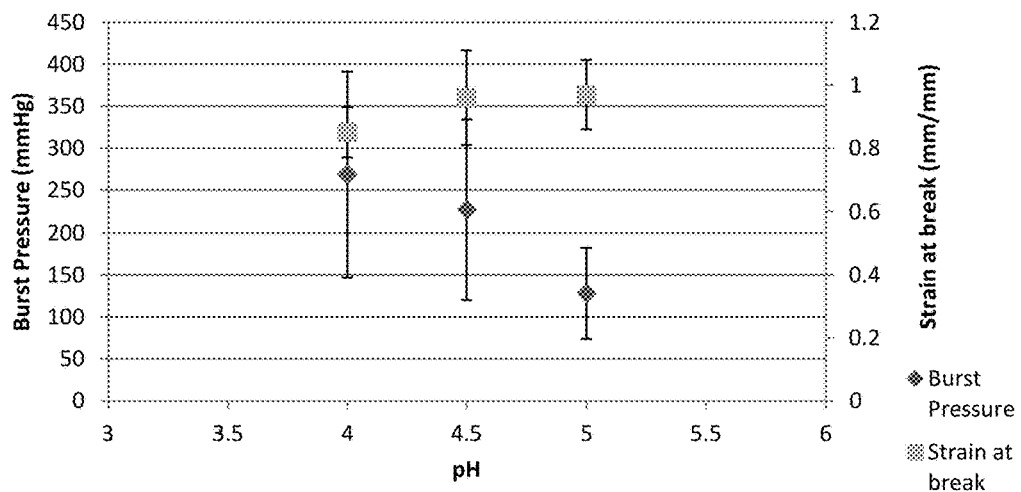
FIG. 2 is a graph showing the burst pressure and strain at break of the double liquid sealant using buffer acetate at different pH values.

FIG. 2 demonstrates the effect of the pH value of the buffer on the burst pressure and the strain of break (critical physical characteristics); higher values of pH yielded on one hand a more flexible sealant and on the other hand an overall weaker sealant.

The reason for this surprising effect is unknown. However, the quantity of the acid in the buffer; as the pH value ascends the acid quantity descends in the buffer, probably lead to a lower dissociation of $CaCO_3$ and finally to a weaker, softer, controllable, more flexible gel.

Figure 3:
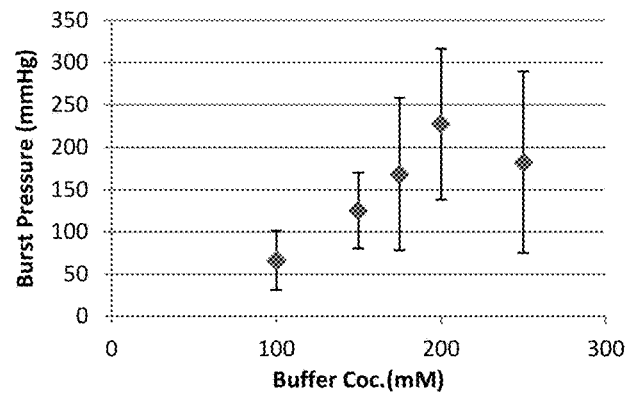
FIG. 3 is a graph showing the burst pressure of the double liquid sealant using buffer acetate at different concentrations.

FIG. 3 demonstrates the effect of the buffer concentration on the burst pressure; higher concentrations of buffer yielded a stronger sealant up to a limit. Above the limit the sealant became brittle and thus the burst pressure values were significantly lowered.

Salt concentration: the crucial issue in this parameter is that the salt concentration must be in excess from the stoichiometric ratio of the salt within the buffer. Otherwise the gel created was very soft and ineffective. This fact was discovered in tension tests that were conducted in order to find the optimal concentration of $CaCO_3$ while maintaining the second component at acetic acid concentration of 0.5%. The concentration of $CaCO_3$ according the stoichiometric ratio was 4.37 mg/ml. However, the gels resulted from concentrations of 3 mg/ml and 4.5 mg/ml were very weak and could not be tested for strain at break because of their mellowness.

Figure 4:
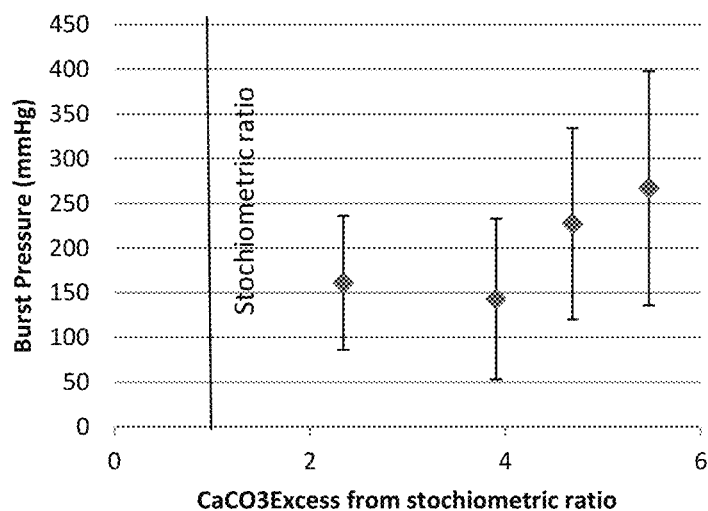
FIG. 4 is a graph showing the burst pressure of the double liquid sealant with various concentrations of CaCO3.
Figure 5:
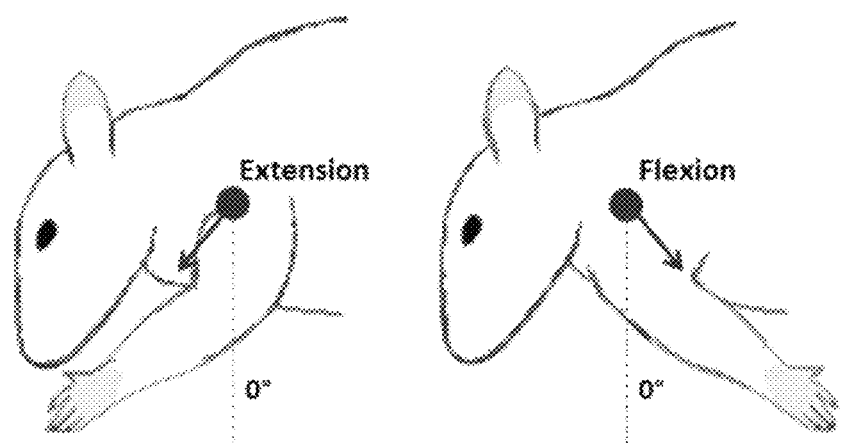
FIG. 5 illustrates the measurement of shoulder full range of motion.

The concentration of $CaCO_3$ according the stoichiometric ratio regarding buffer acetate pH 4.5 200 mM is 6.4 mg/ml. FIG. 4 shows that as long as the salt concentration within the first composition/component is in access (according to the stoichiometry with the buffer) the sealant is stronger and the burst pressure values are higher thus resulting in superior sealants.

Particle size of the salt: The particle size was found to be a very important parameter that affected the reaction time (see Table 1). It was surprisingly discovered that smaller particles enhanced gelation.

TABLE 1

| Particle size (μm) | Gel point (sec) | End of gelation (min) |
| --- | --- | --- |
| 80-100 | 50 | 10 |
| <40 | 20 | 2 |

Table 2 exhibits the results of curing tests conducted on a double liquid composed of two components. The first component: Alginate (20 mg/ml) and $CaNa_2P_2O_7$ (10 mg\ml) in water, second component: Alginate (20 mg/ml) and Acetic acid 0.5% in water. The quality of the resulting gel in both cases was similar i.e. the particle size affected only the gelation time. Another interesting fact is that above a certain concentration the gelation time was not affected any more by particle size, see Table 2.

TABLE 2

| Particle size (μm) | Gel point (sec) | End of gelation (min) |
| --- | --- | --- |
| >100 | 5 | 5 |
| <40 | 5 | 5 |

Further experiments were conducted on a double liquid composed of the components wherein the first component included Alginate (20 mg/ml) and $CaNa_2P_2O_7$ (50 mg\ml) in water, and the second component included Alginate (20 mg/ml) and Acetic acid 0.5% in water. The quality of the gel created in both cases was similar i.e. the particle size affected gelation time. The quality of the gel created in both cases was similar.

Thus particle size variation is used according to the present invention for controlling gelation time.

Salt type: Surprisingly the salt type was also found to be a parameter which affects gelation time and the quality of the gel created (see the table 3, below).

TABLE 3

| | Salt | $Ca^{+2}$ concentration (mg/ml) | Gel point (sec) | End of gelation (min) |
| --- | --- | --- | --- | --- |
| 1 | Ca-stearate | 3.4 | immediate gelation | immediate |
| | $CaCO_3$ | 4 | 15 | 2 |
| 2 | $CaCO_3$ | 8 | 10 | 2 |
| | $CaNa_2P_2O_7$ | 7.7 | 5 | 5 |
| 3 | $Ca_2P_2O_7$ | 2.92 | no gelation | |
| | $CaNa_2P_2O_7$ | 2.92 | 120 | 13 |

Table 3 shows the difference between salts in the gel formation point and the gelation end point.

For Ca-stearate salt, gel formation was faster than for $CaCO_3$ salt, the gel created by Ca-stearate was also surprisingly stronger than the gel created by $CaCO_3$ salt.

For $CaNa_2P_2O_7$ salt, gel formation was faster than for $CaCO_3$ salt, but the end point for gelation was faster for $CaCO_3$ salt. The gel created by $CaCO_3$ salt was also surprisingly stronger than the gel created by $CaNa_2P_2O_7$ salt.

As for $Ca_2P_2O_7$ salt no gelation occurred in the tested concentration while for $CaNa_2P_2O_7$ gelation was apparent at the same concentration.

Buffer type: The type of buffer also affected gelation point and the quality of the gel created (see Table 4, below).

TABLE 4

| Salt | Buffer type | pH | Gel point (sec) | end of gelation (min) |
| --- | --- | --- | --- | --- |
| $CaCO_3$ | Buffer citrate | 4.27 | 20 | 12 |
| $CaCO_3$ | Buffer acetate | 4.5 | 10 | 2 |

Table 4 exhibits the difference in gel formation point and in gelation end point, while the pH values of the buffers are similar.

Also, the gel created by buffer citrate was firm and flexible but contained bubbles while the gel created by buffer acetate was stronger and was free of bubbles.

Example 2: Alginate-Based Formulations Useful for Orthopedic Adhesion Barriers

Ten (10) female Sprague Dawley rats weighing 298 to 419 grams were used in the study. All animal procedures were approved by the Institutional Animal Studies Committee.

The rats were randomly divided into 3 groups, according to the following experimental scheme (Table 5):

TABLE 5

Study design and treatment arms

| Treatment | # of animal | Group |
|---|---|---|
| Saline physiological solution, 1 ml, ready to use | 3 | Control |
| Alginate-Barium containing formulation (Prototype A), prepared aseptically in a separate set of components packed in vials. The final working formulations are mixed and filled in dual syringes (delivery system) in the OR, prior to use | 2 | ALG-A |
| Alginate-Calcium containing formulation (Prototype B), prepared aseptically in a separate set of components packed in vials. The final working formulations are mixed and filled in dual syringes (delivery system) in the OR, prior to use | 5 | ALG-B |

The alginate-barium containing formulation (also denoted herein "ALG-A") comprised a first composition comprising alginate, barium carbonate, and sodium carbonate, and a second composition comprising alginate and acetate buffer.

The alginate-calcium containing formulation (also denoted herein "ALG-B") comprised a first composition comprising alginate and calcium carbonate, and a second composition comprising alginate and acetate buffer.

An open approach to the rotator cuff and proximal humerus was performed using a modified procedure described previously (Peltz C D et al. J Shoulder Elbow Surg. 2012 July; 21(7):873-81; Peltz C D et al. J Orthop Res. 2010 July; 28(7):841-5). Briefly, animals were anesthetized using Isoflurane 1%-2% with an oxygen carrier by nose cone, Ketamine 90 mg/kg/Xylazine 5 mg/kg IM/IP, and Buprenorphine 0.05 mg/kg SC. After sterile preparation and draping, a 2-cm vertical incision was made over the craniolateral aspect of the scapula-humeral joint to expose the deltoid muscle in one of the animal shoulders. The deltoid muscle was then split using the Periost surgical tool to form a subacromial intramuscular pocket. The supraspinatus (SSP) tendon, underlying the deltoid muscle was kept attached to the greater tuberosity, at its original anatomic position. After the approach of an open rotator cuff repair was simulated, the internal surface of the deltoid muscle was scraped repetitively using an RASP tool. Next, either test (alginate) or control (saline) material was applied beneath the operative deltoid muscle. After treatment, the muscle was repositioned at its original anatomic position and closed by 3-4 interrupted sutures (Prolene, 3/0). Finally, the skin was closed using Nylon 3/0 suture. The operated shoulders were immobilized in a flexion position in a plaster cast for 10±2 days. The contralateral shoulders were left uninjured (non-operated) in all 3 groups. Throughout follow-up (F/U) period, animals received postoperative care, including analgesic (Buprenorphine 0.05 mg/kg SC, twice daily for 3 days) and antibiotic (Ceporex 180 mg/kg SC, once daily, for 5 days) treatment, and were monitored for discomfort, distress, and pain.

At the completion of the F/U period (Day 10±2), passive shoulder mechanics were examined in anesthetized animals immediately after the immobilization bandage was removed. The full flexion to full extension angular ranges of motion (ROM) were measured on both operated and non-operated shoulders, using an angle measuring tool. Total angular ROM was then calculated by summing the full flexion and extension ranges. In addition, the severity of the postoperative stiffness was graded using 0-3 scale (0=None; 1=Mild; 2=Moderate; 3=Severe).

The data collected for passive shoulder mechanics measurements in each animal are provided in Table 6.

TABLE 6

Passive Shoulder Mechanics Following Open Surgical Approach to the Rotator Cuff and Proximal Humerus

| % of Total ROM Reduction*** | Total ROM Reduction (degrees) ** | Total ROM (degrees) | | Flexion ROM (degrees) | | Extension ROM (degrees) | | Treatment/ Animal |
|---|---|---|---|---|---|---|---|---|
| | | Operated | Non-operated | Operated | Non-operated | Operated | Non-operated | |
| 63% | 85 | 50 | 135 | 60 | 75 | −10 | 60 | Control 1 |
| 52% | 75 | 70 | 145 | 10 | 70 | 60 | 75 | Control 2* |
| 48% | 55 | 60 | 115 | 65 | 55 | −5 | 60 | Control |
| 0% | 0 | 135 | 135 | 70 | 70 | 65 | 65 | ALG-A 1 |
| 21% | 25 | 95 | 120 | 70 | 60 | 25 | 60 | ALG-A 2 |
| 4% | 5 | 115 | 120 | 65 | 55 | 50 | 65 | ALG-B 1 |
| 8% | 10 | 115 | 125 | 60 | 65 | 55 | 60 | ALG-B 2 |
| 0% | 0 | 115 | 115 | 70 | 55 | 45 | 60 | ALG-B 3 |
| 11% | 15 | 125 | 140 | 70 | 70 | 55 | 70 | ALG-B 4 |
| 0% | 0 | 120 | 120 | 70 | 65 | 50 | 55 | ALG-B 5 |

Control: Untreated shoulders;
ALG-A: Shoulders treated with Alginate-Barium containing formulation;
ALG-B: Shoulders treated with Alginate-Calcium containing formulation.
*In this animal the forelimb was immobilized in extension position (instead of flexion)
** Total ROM Reduction (degrees) = Non-Operated ROM − Operated ROM
***% of Total ROM reduction = (1 − Operated ROM/Non-Operated ROM)*100%

In three control animals, the total mean ROM of the operated shoulders was reduced by 71.7±15.3 degrees (54%±8%), as compared to the non-operated shoulders. In all untreated animals, the severity of the postoperative stiffness of the operated shoulders was defined as severe.

In ALG-A group, one animal showed no change (0%) in the total ROM of the operated vs. non-operated shoulders. No post-operative stiffness of the operated shoulders was found in this animal (Grade: 0). In another animal from the same group, reduction of 25 degrees (21%) in the total ROM of the operated vs. non-operated shoulders was recorded, and the postoperative stiffness of the operated shoulder was graded as mild.

Five animals in ALG-B group showed total mean ROM reductions of 6.0±6.5 degrees (5%±5%) on the operated vs.

non-operated shoulders. In these animals, postoperative stiffness of the operated shoulders was identified as none to very mild.

Figure 6A:
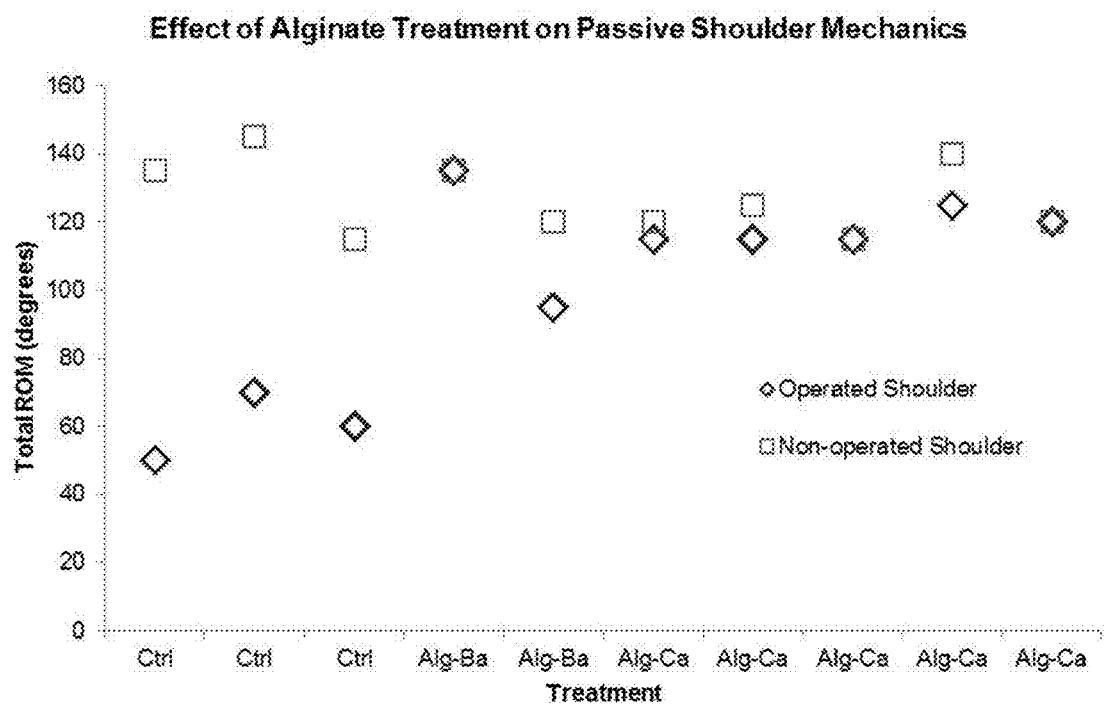
FIGS. 6A-C depict the effect of alginate adhesion barrier on passive shoulder mechanics in rat.
Figure 6B:
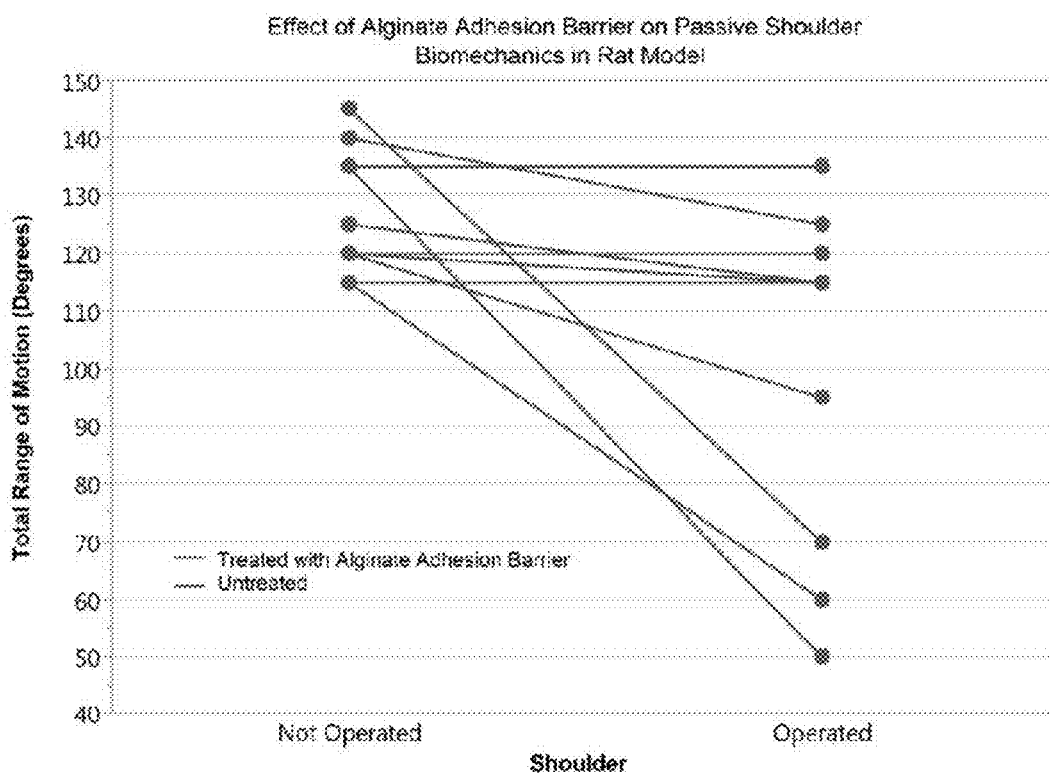
Figure 6C:
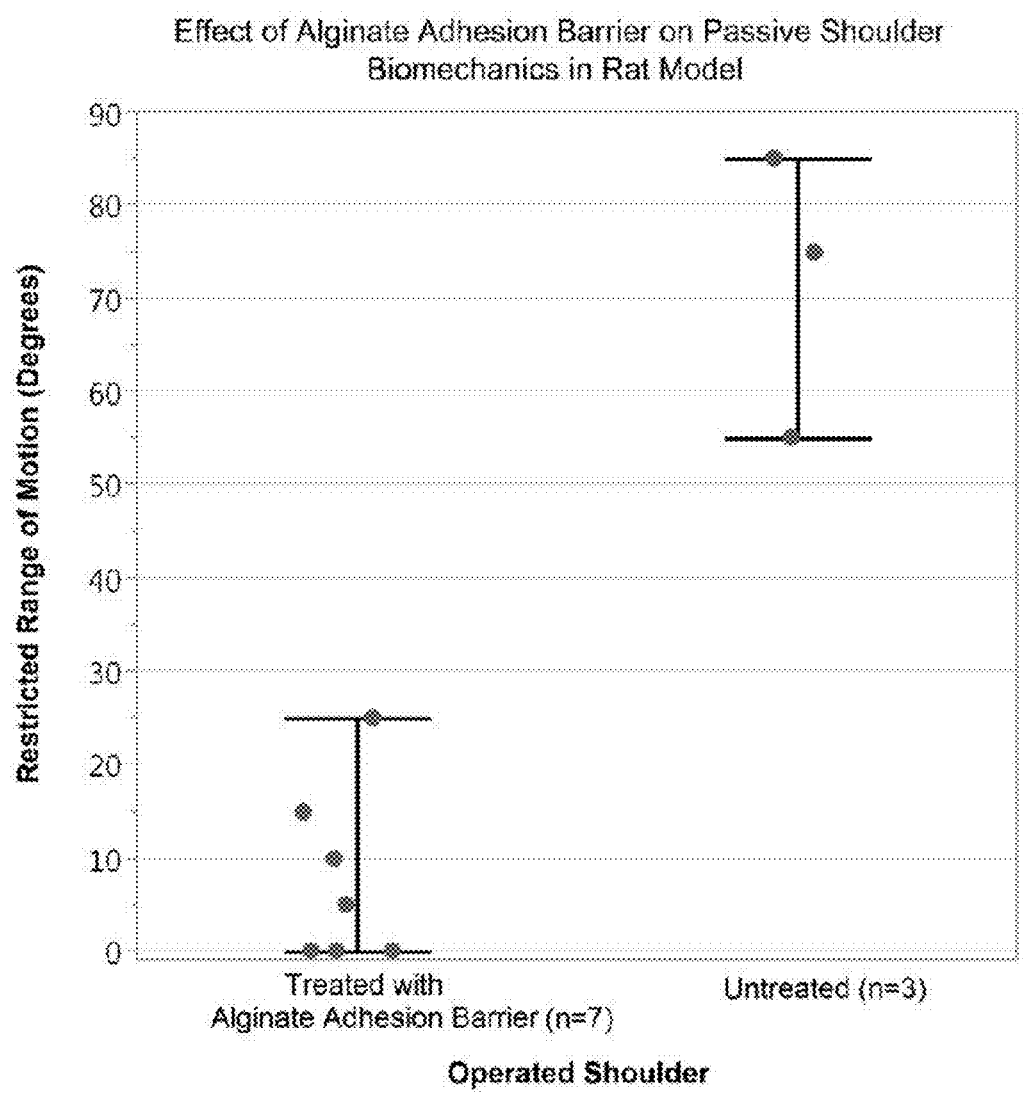

Graphical presentation of the total, flexion and extension ROM outcomes on operated versus non-operated shoulders in all alginate treated and untreated animals are provided in FIG. 6.

In this study, an experimental model of the deltoid muscle injury in the rat subacromial area with following limb immobilization was used to imitate open proximal humerus surgery, such an experimental procedure is commonly associated with formation of postoperative adhesions, stiffness and restricted mobility of the operated shoulder. In common clinical practice, the key measures for assessment of the impairments in the shoulder function and mobility deficits are shoulder range of motion (ROM) (Kelley M J, et al. J Orthop Sports Phys Ther. 2013 May; 43(5):A1-31). In fact, in the present study the findings of notable postoperative shoulder stiffness and restricted passive ROM obtained in control animals support the applicability of the experimental model for further evaluation of adhesion barrier systems. In one of the control animals, the operated forelimb was immobilized in opposite position (extension instead of flexion), leading to the notable loss of the ROM in opposite direction, as compared to another control animal. In agreement with Liu et al (Chin Med J (Engl). 2011 December; 124(23):3939-44), the position of forelimb fixation is highly correlated with the direction of the shoulder immobility post-immobilization. Nevertheless, when measuring the total ROM, by summing flexion and extension, the shoulder mobility deficits were consistent in both control animals.

In alginate-treated animals, as compared to controls, preserved passive mobility and negligible shoulder stiffness were noted post-operatively, indicating a potential ability of the alginate material to prevent adhesion formation in the shoulder tissues. Alginate gels have been previously suggested to reduce adhesions after abdominal and colon surgeries in rat model (Chaturvedi, 2013, ibid. and Chaturvedi, 2014, ibid). In these studies the alginate gels were formed in the proximity, but were not attached, to the peritoneal wall or colon; thus potentially constituting a risk of the gel migration from the target tissue.

Figure 7:
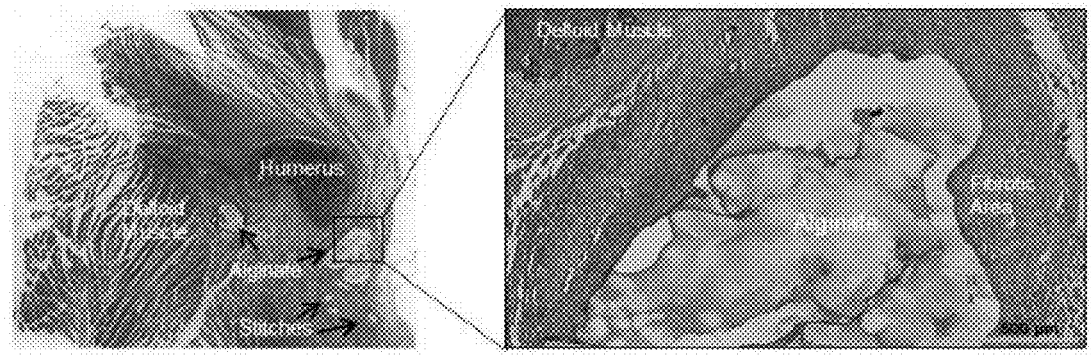
FIG. 7 shows histological evidence of alginate adhesion barrier in rat shoulder.
Figure 7:
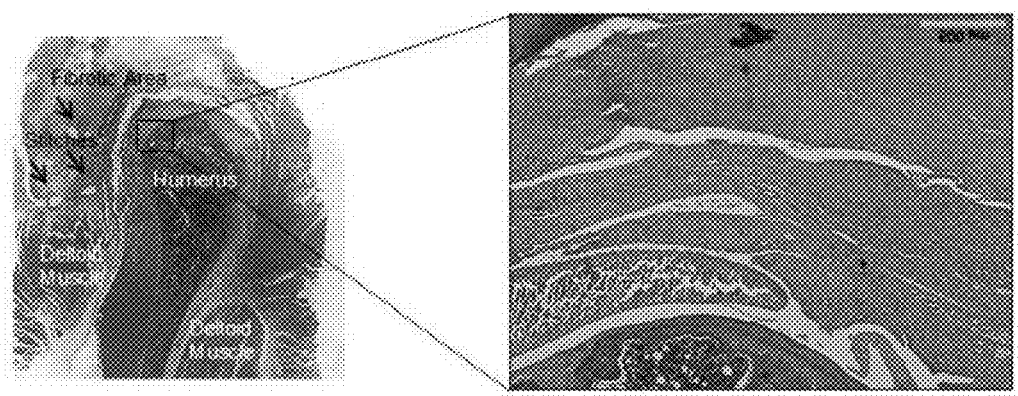

The alginate formulations of the present invention adhere to the target tissue area and are, therefore, more effective in formation of a stable adhesion barrier (FIG. 7). This example demonstrated the feasibility of two alginate formulations in providing an adhesion barrier between the deltoid muscle and the underlying rotator cuff and reduction of postoperative stiffness, after an open surgical approach to the proximal humerus in a rat model.

In the current series of experiments in rat, at Day 10 post-operation the histological findings demonstrate normal tissue response, reflected by presence of fibrotic tissue at a moderate extent and no tissue necrosis in the alginate-treated animals. In addition, alginate material residues were observed in the tissue, within the deltoid muscle layers at the operation site. More extensive fibrotic reaction, which may reflect a higher extent of post-operative adhesions, was noted in the control, untreated animals (FIG. 7).

Example 3: The Mechanical Properties of the Adhesive

Alginate solution (68 mg/ml) was mixed with different concentrations of inactive cross linker and trigger. The different systems were tested for burst pressure on fresh swine colon. Burst pressure of at least 75-200 mmHg was reached.

In order to estimate the effect of trigger concentration on the mechanical properties of the adhesive, various buffer concentrations in the alginate\trigger solution were tested. Samples were tested for burst pressure on fresh swine colon.

The results showed that buffer concentrations in the range of 100-700 mM can act as effective triggering compound with a burst pressure of 25-220 mmHg.

What is claimed is:

1. A kit comprising: a first component and a second component, said first component comprises a crosslinkable polysaccharide and a multivalent cation salt at a concentration ratio (mg/ml) of 30:1 to 1:60, said second component comprises a crosslinkable polysaccharide and a buffer, said buffer has a pH value of between 2 to 6 and comprises (i) an acid and (ii) its acid addition salt.

2. The kit of claim 1, wherein said crosslinkable polysaccharide is alginate.

3. The kit of claim 1, wherein said crosslinkable polysaccharide and said multivalent cation salt are at a concentration ratio (mg/ml) of 1:1 to 1:4.

4. The kit of claim 1, wherein said multivalent cation salt is selected from:
a calcium salt selected from the group comprising: $CaCO_3$, $(C_{17}H_{35}COO)_2Ca$, $CaNa_2P_2O_7$, $Ca_2P_2O_7$, or any combination thereof;
a multivalent cation salt present at a concentration of 20 to 40 mg/ml within said first component; and
a particle size between 0.1 microns and 150 microns.

5. The kit of claim 1, wherein said crosslinkable polysaccharide is present at a concentration of 5 to 100 mg/ml within said first component and crosslinkable polysaccharide is present at a concentration of 5 to 100 mg/ml within said second component.

6. The kit of claim 1, wherein said buffer has a concentration selected from: between 1 to 2000 mM and 100 to 500 mM.

7. The kit of claim 1, wherein said buffer is selected from a buffer having a pH value of between 4 to 5 and a buffer comprises acetic acid and sodium acetate salt.

8. The kit of claim 1, wherein the concentration of said multivalent cation salt in said first component is 1.5 to 10 times higher than the stoichiometric ratio of said buffer gent having a concentration of between 100 to 500 mM.

9. The kit of claim 1, wherein said multivalent cation salt is $CaCO_3$ at a concentration of 20 to 40 mg/ml, said crosslinkable polysaccharide is present at a concentration of 10 to 30 mg/ml in said first component, said crosslinkable polysaccharide is present at a concentration of 10 to 30 mg/ml in said second component, said buffer is buffer acetate having a pH value between 4 to 5 and a concentration of between 150 to 300 mM.

10. The kit of claim 1, further comprising an instruction manual, optionally wherein said instruction manual provides instruction with respect to quantities of said first component and said second component to be applied, further optionally wherein said instruction manual provides a spectrum of gelation time, wherein said gelation time is affected by the particle size of said calcium salt, the particular calcium salt, the type of buffer, the pH value of said buffer, or any combination thereof.

11. The kit of claim 1, wherein the combination of said first component and/or said second component have a viscosity of between 100 cP and 100000 cP.

12. A method for forming a sealant, comprising contacting a first composition and a second composition, wherein said first composition comprises a crosslinkable polysaccharide and a multivalent cation salt at a concentration ratio (mg/ml) of 30:1 to 1:60, said second composition comprises a crosslinkable polysaccharide and a buffer, said buffer has a pH value of between 2 to 6 and comprises an acid and its acid addition salt, thereby forming a sealant.

13. The method of claim 12, wherein said crosslinkable polysaccharide and said multivalent cation salt are at a concentration ratio (mg/ml) of 1:1 to 1:4 or wherein said crosslinkable polysaccharide is present at a concentration of 5 to 100 mg/ml within said first composition and said crosslinkable polysaccharide is present at a concentration of 5 to 100 mg/ml in said second composition, optionally wherein said crosslinkable polysaccharide is alginate.

14. The method of claim 12, wherein said multivalent cation salt is selected from:
 a calcium salt selected from the group comprising: $CaCO_3$, $(C_{17}H_{35}COO)_2Ca$, $CaNa_2P_2O_7$, $Ca_2P_2O_7$, or any combination thereof;
 a multivalent cation salt present at a concentration of 20 to 40 mg/ml within said first component;
 a particle size between 0.1 microns and 150 microns; and
 a multivalent cation salt having a concentration in said first composition of 1.5 to 10 times higher than the stoichiometric ratio of said buffer having a concentration of between 100 to 500 mM.

15. The method of claim 12, wherein said buffer is selected from:
 a buffer has a concentration of between 1 to 2000 mM;
 a buffer having a pH value of between 4 to 5; and
 a buffer having acetic acid and sodium acetate salt.

16. The method of claim 12, wherein said multivalent cation salt is calcium salt is $CaCO_3$ at a concentration of 20 to 40 mg/ml, said crosslinkable polysaccharide is present at a concentration of 10 to 30 mg/ml in said first composition, said crosslinkable polysaccharide is present at a concentration of 10 to 30 mg/ml in said second composition, said buffer is buffer acetate having a pH value between 4 to 5 and a concentration of between 150 to 500 mM.

17. The method of claim 12, wherein said forming a sealant further comprises controlling gelation time, wherein said pH value of less than 4.5 increases gelation time, wherein smaller particle size of said bivalent cation salt decreases gelation time or wherein said forming a sealant is forming a sealant having a viscosity of between 100 cP and 100000 cP.

18. A sealant or an adhesion barrier produced by mixing a first composition comprising a crosslinkable polysaccharide and a bivalent cation salt at a concentration ratio (mg/ml) of 30:1 to 1:60 and a second composition comprising a crosslinkable polysaccharide and a buffer, said buffer has a pH value of between 2 to 6 and comprises an acid and its acid addition salt.

19. A method comprising the step of:
 (a) providing a first composition and a second composition, said first composition comprises a crosslinkable polysaccharide and a multivalent cation salt at a concentration ratio (mg/ml) of 30:1 to 1:60, said second composition comprises a crosslinkable polysaccharide and a buffer, said buffer has a pH value of between 2 to 6 and comprises an acid and its acid addition salt, and optionally mixing said first composition and said second composition; and
 (b) applying said first composition and said second composition to the target site thereby forming an adhesion barrier in situ, wherein said adhesion barrier adheres to said target site, thereby, inhibiting, or reducing fibrosis, scarring, and/or adhesion in said target site.

20. The method of claim 19 for inhibiting, or reducing fibrosis, scarring, and/or adhesion in a target site, or for securing or holding a graft in a target site.

* * * * *